US012496189B2

(12) United States Patent
Singh et al.

(10) Patent No.: US 12,496,189 B2
(45) Date of Patent: Dec. 16, 2025

(54) PACKAGING-INTEGRATED MANUALLY ACTUATED INTRAOCULAR LENS CARTRIDGE

(71) Applicant: Alcon Inc., Fribourg (CH)

(72) Inventors: Sudarshan B. Singh, Euless, TX (US); Todd Taber, Keller, TX (US); Douglas Brent Wensrich, Bedford, TX (US); Yinghui Wu, Cedar Hill, TX (US); Trevor Haney, Jenison, MI (US); Andrew Check, Kalamazoo, MI (US); Justin Benacquisto, New Baltimore, MI (US); Joe Marietta, Kalamazoo, MI (US); Jonathan Penrod, Kalamazoo, MI (US); Tim LaRoy, Kalamazoo, MI (US); Bryce Porter, Kalamazoo, MI (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/444,535

(22) Filed: Feb. 16, 2024

(65) Prior Publication Data

US 2024/0245505 A1 Jul. 25, 2024

Related U.S. Application Data

(63) Continuation of application No. 16/999,434, filed on Aug. 21, 2020, now Pat. No. 11,931,247.

(Continued)

(51) Int. Cl.
*A61F 2/16* (2006.01)

(52) U.S. Cl.
CPC ............ *A61F 2/1691* (2013.01); *A61F 2/167* (2013.01); *A61F 2/1678* (2013.01); *A61F 2002/1683* (2013.01)

(58) Field of Classification Search
CPC ...... A61F 2/1691; A61F 2/167; A61F 2/1678; A61F 2/1664; A61F 2002/1683; A61F 2/1662
See application file for complete search history.

(56) References Cited

U.S. PATENT DOCUMENTS

| | | | | |
|---|---|---|---|---|
| 2006/0142780 A1* | 6/2006 | Pynson ................. | A61F 2/1662 606/107 |
| 2010/0305577 A1* | 12/2010 | Muchhala ............. | A61F 2/1678 606/107 |

(Continued)

*Primary Examiner* — Brigid K Byrd
(74) *Attorney, Agent, or Firm* — Patterson + Sheridan, LLP

(57) ABSTRACT

Systems, methods, and apparatuses for storing and/or shipping an intraocular lens (IOL) cartridge are provided. A system comprises the IOL cartridge comprising a nozzle, a compartment comprising an IOL, and a dial disposed adjacent to the compartment. The nozzle is in fluid communication with the compartment, and the dial is configured to fold the IOL upon rotation of the dial. The IOL cartridge further comprises a plunger case in fluid communication with the compartment, wherein a plunger is movably disposed within the plunger case. The system further comprises a packaging comprising a base, wherein the IOL cartridge is disposed within the base; a first removable cover configured to cover a first portion of the IOL cartridge; and a second removable cover configured to cover a second portion of the IOL cartridge, wherein the second removable cover is locked in place when the dial is in a non-rotated position.

20 Claims, 8 Drawing Sheets

Related U.S. Application Data

(60) Provisional application No. 63/035,148, filed on Jun. 5, 2020, provisional application No. 62/890,859, filed on Aug. 23, 2019.

(56) References Cited

U.S. PATENT DOCUMENTS

| | | | | |
|---|---|---|---|---|
| 2012/0158007 | A1* | 6/2012 | Brown | A61F 2/1691<br>606/107 |
| 2013/0226193 | A1* | 8/2013 | Kudo | A61F 9/0008<br>606/107 |
| 2014/0200588 | A1* | 7/2014 | Anderson | A61F 2/1675<br>606/107 |
| 2016/0051359 | A1* | 2/2016 | Esguerra | A61F 2/1451<br>606/107 |

* cited by examiner

PACKAGING-INTEGRATED MANUALLY ACTUATED INTRAOCULAR LENS CARTRIDGE

CROSS-REFERENCE TO RELATED APPLICATIONS

This application is a continuation of U.S. Non-Provisional patent application Ser. No. 16/999,434, filed Aug. 21, 2020, which claims the benefit of U.S. Provisional Application No. 63/035,148, filed Jun. 5, 2020, and U.S. Provisional Application No. 62/890,859, filed Aug. 23, 2019. Each of the aforementioned applications is incorporated by reference herein in its entirety, and each is hereby expressly part of this specification.

TECHNICAL FIELD

The present disclosure generally relates to eye surgery and, more particularly, some embodiments may generally relate to systems, methods, and apparatuses for removably attaching a drive mechanism handpiece to a manually actuated intraocular lens (IOL) cartridge that is integrated within packaging.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be pre-loaded in the insertion tool. In other instances, a separate bay may be loaded into the insertion tool. The plunger may engage the IOL to advance the IOL from the bay, through a nozzle, and into the eye.

SUMMARY

In an exemplary embodiment, the present disclosure provides a system for storing and/or shipping an intraocular lens (IOL) delivery device. The system comprises the IOL cartridge. The IOL cartridge comprises a compartment comprising an IOL. The IOL cartridge further comprises a dial disposed adjacent to the compartment, wherein an inner surface of the dial is exposed to the compartment. The dial is configured to fold the IOL upon rotation of the dial. The IOL cartridge further comprises a plunger case in fluid communication with the compartment, wherein a plunger is movably disposed within the plunger case. The IOL cartridge is configured to removably attach to a handpiece. The system may further include a packaging configured to enclose the IOL cartridge, and the packaging may be further configured to prevent removal of the IOL cartridge prior to rotation of the dial of the IOL cartridge. The packaging may further comprise a base, wherein the IOL cartridge is disposed within the base; a first removable cover configured to cover a first portion of the IOL cartridge; and a second removable cover configured to cover a second portion of the IOL cartridge. The dial may further comprise at least one arm, the second removable cover may comprise at least one prong configured to extend under the at least one arm of the dial, and the at least one arm may prevent removal of the at least one prong and the second removable cover when the dial is in the non-rotated position.

In another exemplary embodiment, the present disclosure provides a system for storing and/or shipping an IOL cartridge. The IOL cartridge may comprise a compartment configured to contain an IOL. The IOL cartridge further comprises a dial disposed adjacent to the compartment, wherein an inner surface of the dial is exposed to the compartment. The dial is configured to fold the IOL upon rotation of the dial. The IOL cartridge further comprises a plunger case in fluid communication with the compartment, wherein a plunger is movably disposed within the plunger case. The IOL cartridge is configured to removably attach to a handpiece. The system further comprises a packaging comprising a base, wherein the IOL cartridge is disposed within the base; a first removable cover configured to cover a first portion of the IOL cartridge; and a second removable cover adjacent to the first removable cover, the second removable cover configured to cover a second portion of the IOL cartridge, wherein the second removable cover is locked in place by the dial in a non-rotated position.

In another exemplary embodiment, the present disclosure provides a method for delivery of an IOL. The method comprises opening a first cover of packaging to expose a first portion of an IOL cartridge contained within a base of the packaging. The IOL cartridge comprises a compartment comprising the IOL. The method further comprises rotating a dial of the IOL cartridge to fold the IOL and unlock a second cover covering a second portion of the IOL cartridge; opening the second cover; and removing the IOL cartridge from the base of the packaging.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
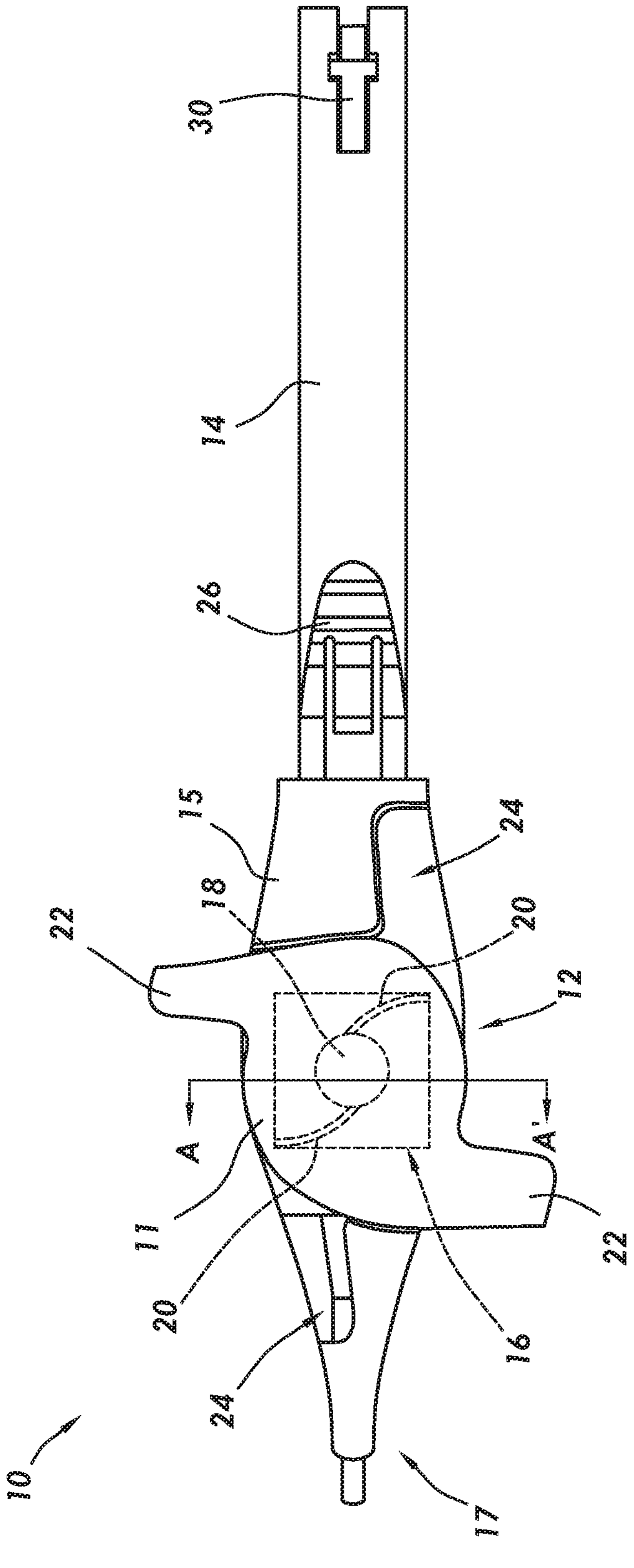
FIG. 1 illustrates a top view of a preloaded IOL cartridge with a dial in an initial non-rotated position, in accordance with some embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide a manually actuated intraocular lens cartridge ("IOL cartridge") that is integrated within packaging. The IOL cartridge may initially be contained in the packaging for storage and/or shipping. The IOL cartridge includes a dial that is manually rotated. Manual rotation of the dial actuates a folding mechanism of the IOL cartridge and releases the IOL cartridge from the packaging. The IOL cartridge may be a preloaded cartridge that is preloaded with the IOL. The IOL cartridge may be part of a modular delivery system that includes a universal interface for removable attachment to various handpieces that include different types of drive mechanisms.

Particular embodiments of the present disclosure allow interchangeability between different handpieces such as disposable and reusable handpieces, and the IOL cartridge. The disposable handpieces may include drive mechanisms that are not electrically powered. The reusable handpieces may include non-powered drive mechanisms (e.g., simply manual pushing or screwing; manually actuated via a fluid or a resilient member such as a spring) as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure allow assembling of the handpiece to the IOL cartridge, delivering the IOL, and disengaging the handpiece from the used IOL cartridge, if needed. The universal interface allows the different types of handpieces to be easily paired to and utilized with the IOL cartridge for IOL implantation. After the IOL implantation, the IOL cartridge can be easily detached from the reusable handpiece.

The handpiece may be secured to the IOL cartridge by sliding an end of the handpiece over the plunger case of the IOL cartridge. In certain embodiments, the IOL cartridge may include a clip that presses against a housing of the handpiece to secure the handpiece to the IOL cartridge. Once secured, the IOL may be delivered into an eye. After the IOL delivery has been completed, the handpiece may be disconnected from the used IOL cartridge by moving the clip away from the housing of the handpiece and sliding the IOL cartridge out from within the handpiece.

FIG. 1 illustrates a top view of an IOL cartridge 10 with a dial 11 in an initial non-rotated position in accordance with some embodiments of the present disclosure. The IOL cartridge 10 may include a compartment 12 in fluid communication with a plunger case 14. The compartment 12 may be disposed within a housing 15 of the IOL cartridge 10, and the plunger case 14 may extend from the housing 15.

A nozzle 17 may extend from the housing 15. The nozzle 17 may be in fluid communication with the compartment 12. The compartment 12 may be preloaded or contain an IOL 16. The IOL 16 may be delivered through the nozzle 17.

The IOL 16 may include a lens portion 18 and haptic extensions 20. The haptic extensions 20 may be side struts (or other suitable extensions) extending from the lens portions 16 that may stabilize the IOL 16 when it may be disposed within the patient's eye. It should be understood that the IOL 16 is merely exemplary and that techniques disclosed herein may be used with any suitable IOL. For example, a modular IOL (not shown) that includes a lens portion disposable in a base with haptic extensions can also be used.

The dial 11 may be rotated to fold the IOL 16. The dial 11 may include arms 22 for grasping by a user. The IOL cartridge 10 may include pockets 24 to receive the arms 22 of the dial 11 upon rotation (e.g., 90° counterclockwise) of the dial 11.

A clip 26 may extend from the housing 15 of the IOL cartridge 10 and extend over the plunger case 14. The clip 26 may be made from a flexible material such as plastic, for example. The clip 26 may be utilized as a coupling mechanism to removably couple the IOL cartridge 10 to a handpiece (not shown).

The plunger case 14 may be a hollow and rigid member that may house a plunger 30 which may be movably disposed within the plunger case 14. As illustrated, only a tail end of the plunger 30 is shown. The plunger 30 extends longitudinally within the plunger case 14 and may be driven forward through the compartment 12 to deliver the IOL 16 through the nozzle 17.

Figure 2:
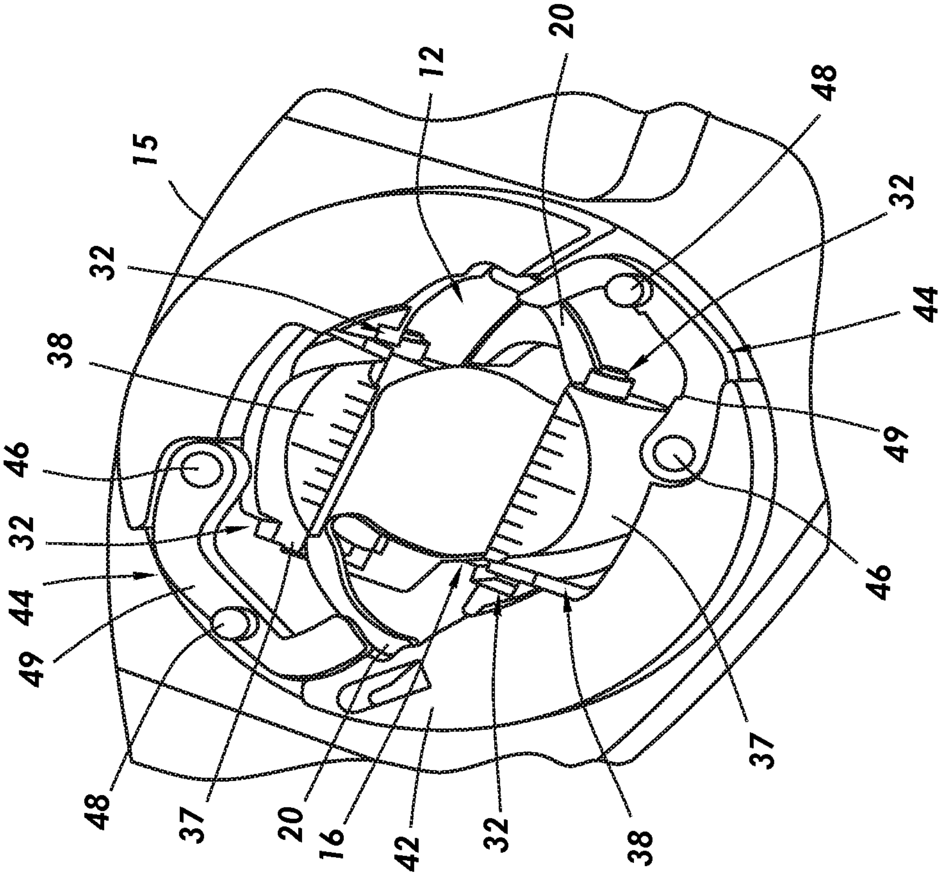
FIG. 2 illustrates a cut away view of components beneath a dial of the preloaded IOL cartridge of FIG. 1, in accordance with some embodiments of the present disclosure.

FIG. 2 illustrates a cutaway top view of the compartment 12 in accordance with some embodiments of the present disclosure. The dial 11 (e.g., shown on FIG. 1) is not shown in order to illustrate an unobstructed top view of components positioned directly below the dial 11.

In some embodiments, the compartment 12 may contain edge rollers 38 that are pivotably disposed within the compartment 12. The edge rollers 38 may be used to fold the IOL 16. As illustrated, the IOL 16 may be disposed between the edge rollers 38. The edge rollers 38 may include top pins 37 extending laterally from upper portions of the edge rollers 38. The top pins 37 are positioned to contact an inner surface (not shown) of the dial 11 (e.g., shown on FIG. 1), upon rotation of the dial 11. Rotation of the dial 11 causes the edge rollers 38 to rotate upward and inward, thereby folding the IOL 16. The compartment 12 may also include recesses 32 that are pivot points for the edge rollers 38. The dial 11 may be disposed directly above the compartment 12 and may be supported by an internal portion 42 of the housing 15. The internal portion 42 encompasses, surrounds, or generally defines boundaries for the compartment 12.

Compression arms 44 may be pivotably coupled to the internal portion 42 of the housing 15 via connecting pins 46 and may extend into the compartment 12. The compression arms 44 may include protrusions 48 extending from an upper surface 49 of the compression arms 44 to contact an inner surface (not shown) of the dial 11 (e.g., shown on FIG. 1) upon rotation of the dial 11. Rotation of the dial 11 causes the compression arms 44 to move inward thereby folding or compressing the haptic extensions 20 of the IOL 16. The inward movement of the compression arms 44 may be simultaneous with the inward and upward movement of the edge rollers 38 to fold and compress the IOL 16 for delivery into an eye.

Figure 3:
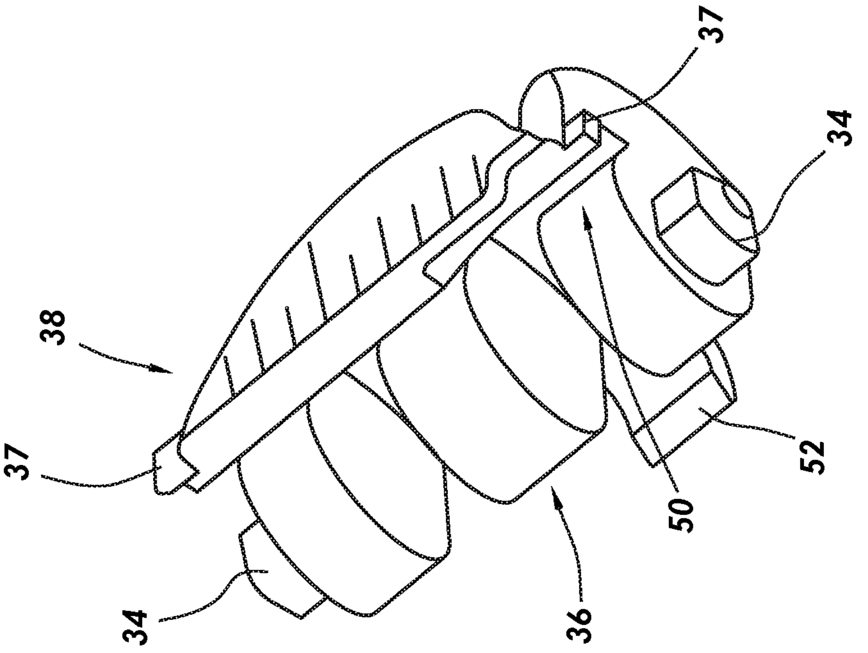
FIG. 3 illustrates a side perspective view of an edge roller contained within the compartment of the preloaded IOL cartridge of FIGS. 1 and 2.

FIG. 3 illustrates a side perspective view of an edge roller 38 in accordance with some embodiments of the present disclosure. The edge roller 38 may include a cam 36 extending along a length of the edge roller 38. The cam 36 may include cam pins 34 that allow the edge roller 38 to rotate within the recesses 32 (e.g., shown on FIG. 2). The top pins 37 may be moved inward by the inner surface of the dial 11 (shown on FIG. 1). The edge roller 38 may also include a recess 50. A portion of the IOL 16 (shown on FIG. 2) may be disposed in the recess 50 of each edge roller 38. The recess 50 may extend along a length of the edge roller 38. As the edge roller 38 rotates upward and inward, via the cam pins 34, the IOL 16 folds. Additionally, the edge roller 38 may include a tail portion 52 that may prevent backward rotation of the edge roller 38 as the edge roller 38 is rotated upward and inward, upon rotation of the dial 11 (e.g., shown on FIG. 1).

Figure 4:
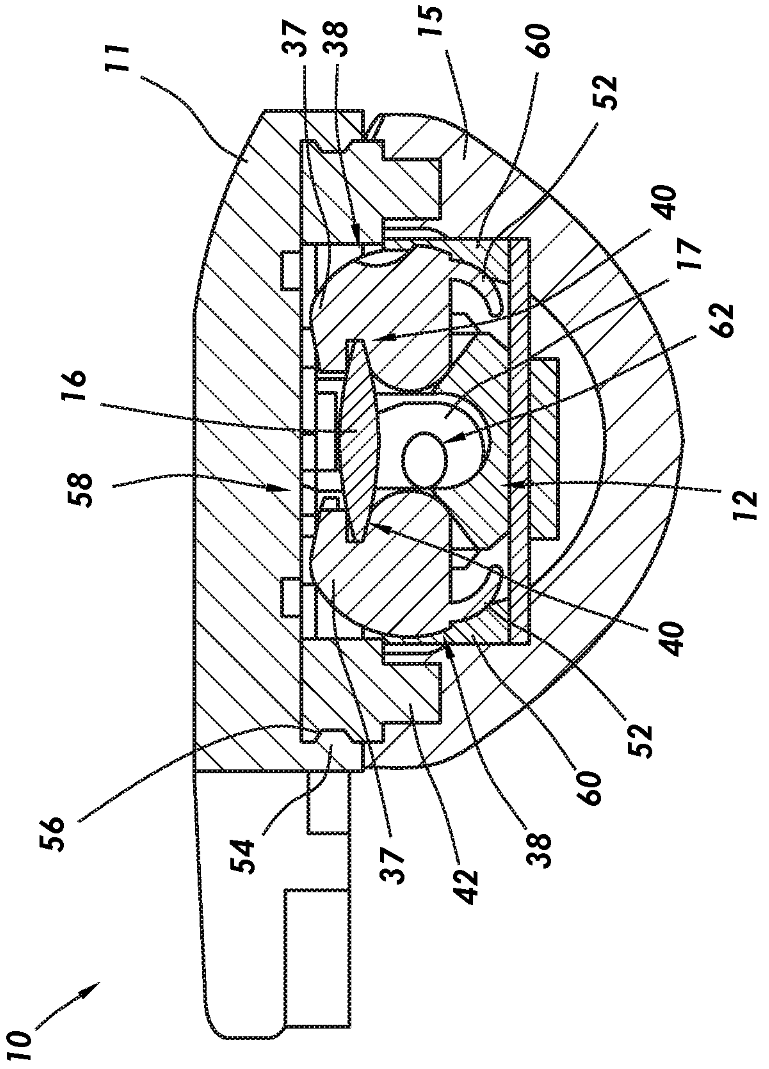
FIG. 4 illustrates a cross-sectional view of a compartment of the preloaded IOL cartridge of FIG. 1 with an IOL in a non-folded state.

FIG. 4 illustrates a cross-sectional view of the IOL cartridge 10 taken along line A-A' of FIG. 1, in accordance with some embodiments of the present disclosure. The dial 11 may be disposed directly above the compartment 12 and may be supported by the internal portion 42 of the housing 15 of the IOL cartridge 10. The dial 11 may rotate about the internal portion 42 and may include a lip 54 that corresponds with a groove 56 of the portion 42 to secure the dial 11 to the portion 42 of the housing 15. An inner surface 58 of the dial 11 may be exposed to the compartment 12. The inner surface 58 may be contoured to contact or mate with the top pins 37 of the edge rollers 38, upon rotation of the dial 11. The edge rollers 38 may rotate upward and inward, upon rotation of the dial 11, thereby folding the IOL 16.

The inner surface 58 may also be contoured to contact or mate with the protrusions 48 (e.g., shown on FIG. 2) of compression arms 44 (e.g., shown on FIG. 2), upon rotation of the dial 11. Rotation of the dial 11 moves the compression arms 44 inward to compress the haptic extensions 20 (e.g., shown on FIG. 2) of the IOL 16.

The tail portions 52 contact and ride upward along tapered walls 60 of the compartment 12. The tail portions 52 may prevent backward rotation of the edge rollers 38 as the edge rollers 38 are rotated upward, upon rotation of the dial 11. A passage 62 may extend from the compartment 12 and through the nozzle 17 to receive the IOL 16 in a folded state.

Figure 5:
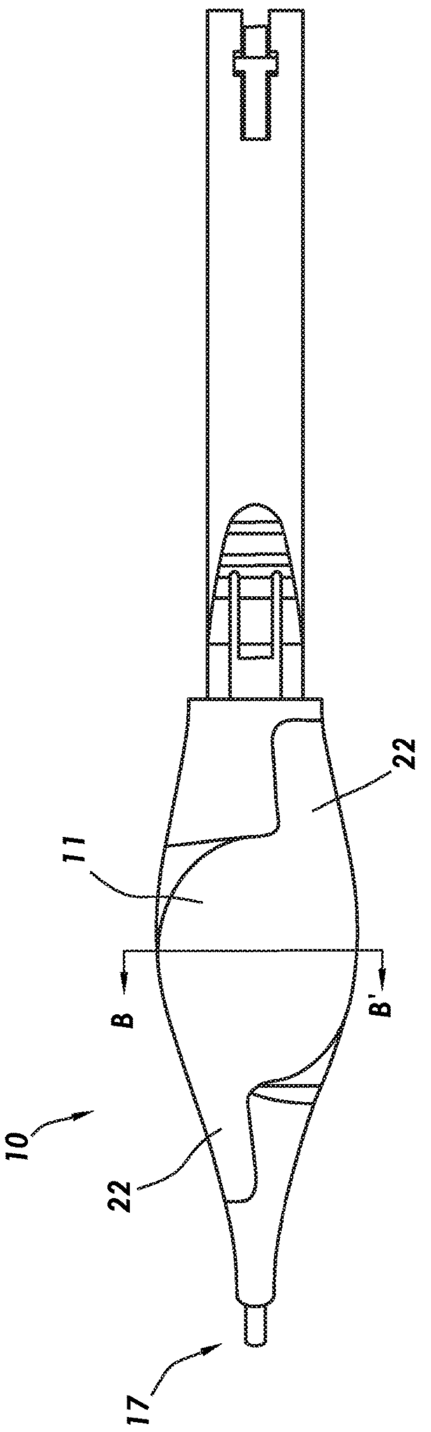
FIG. 5 illustrates a top view of a preloaded IOL cartridge with a dial in a rotated position, in accordance with some embodiments of the present disclosure.

FIG. 5 illustrates a top view of the IOL cartridge 10 with the dial 11 in a rotated position, in accordance with some embodiments of the present disclosure. As shown, the dial 11 has been rotated (e.g., 90°) thereby causing the arms 22 to move into the pockets 24 (shown on FIG. 1). Rotation of the dial 11 also folds the IOL 16 (e.g., shown on FIG. 2), as described above with reference to FIGS. 2-4.

Figure 6:
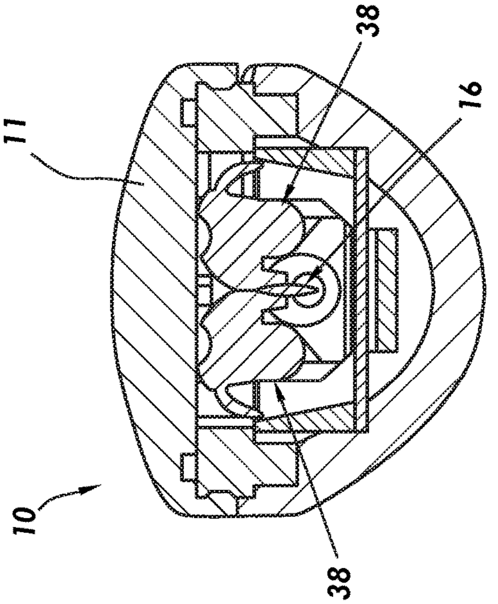
FIG. 6 illustrates a cross-sectional view of the preloaded IOL cartridge of FIG. 5 with a folded IOL, in accordance with some embodiments of the present disclosure.

FIG. 6 illustrates a cross-sectional view of the IOL cartridge 10 taken along line B-B' of FIG. 5, in accordance with some embodiments of the present disclosure. As shown, the dial 11 has rotated to cause the edge rollers 38 to have rotated to fold the IOL 16. Also, the compression arms 44 (e.g., shown on FIG. 2) have rotated inward to compress the haptic extensions 20 (shown on FIG. 2) of the IOL 16.

Figure 7:
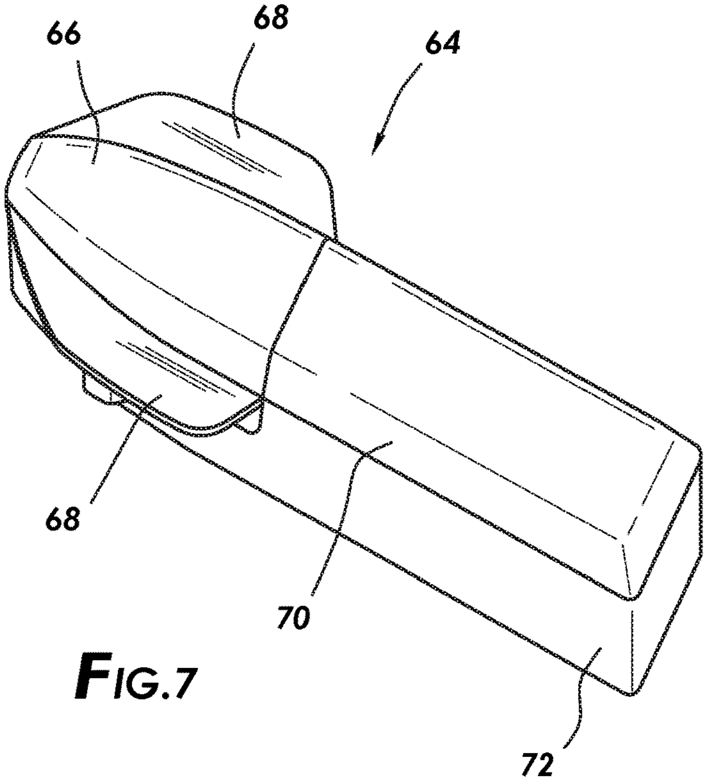
FIG. 7 illustrates a packaging for the preloaded IOL cartridge of FIG. 1, in accordance with some embodiments of the present disclosure.

FIG. 7 illustrates a top perspective views of a packaging 64 used for storing and/or shipping an IOL cartridge 10 (e.g., as shown on FIG. 1) in accordance with some embodiments of the present disclosure. The packaging 64 may be made of plastic and may include a first cover 66 that may include lateral projections 68 to facilitate (e.g., grasping by a user) removal of the first cover 66. A second cover 70 may be positioned adjacent to the first cover 66. Both the first cover 66 and the second cover 70 may be aligned longitudinally on top of a base 72 that may contain the IOL cartridge 10. Both the first cover 66 and the second cover 70 may be at least partially lifted or removed from the base 72. The first cover 66 and the second cover 70 can provide seals to prevent contamination of the IOL cartridge 10 disposed within, which may include a pre-loaded IOL 16, during shipping and/or storage.

Figure 8:
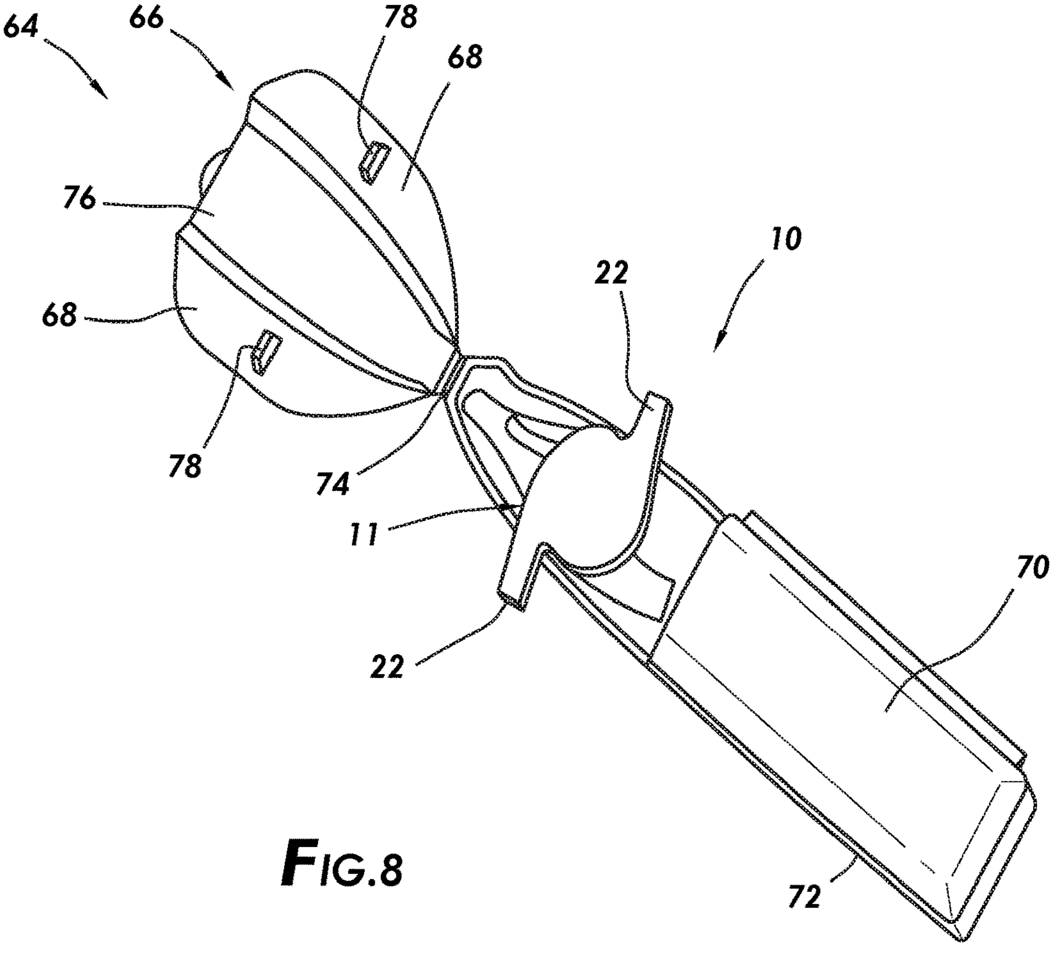
FIG. 8 illustrates a top view of the packaging of FIG. 7 with a first cover removed to expose a dial of the IOL cartridge, in accordance with some embodiments of the present disclosure.

FIG. 8 illustrates a top perspective view of the packaging 64 with the first cover 66 opened, in accordance with some embodiments of the present disclosure. The first cover 66 may be removed (e.g., pulled away) from the base 72 to expose the dial 11 of the IOL cartridge 10. The dial 11 may be in the initial non-rotated position. The dial 11 may include the arms 22 that may project outward from the packaging 64, as shown. The arms 22 can be utilized for grasping to rotate the dial 11. While the first cover 66 remains on the base 72, the arms 22 may extend outward beneath the lateral projections 68. Manual rotation of the dial 11 folds the IOL 16 and allows the IOL cartridge 10 to be released from the packaging 64, as will be further discussed in the following paragraphs.

A hinge 74 may pivotably couple the first cover 66 to the base 72. The hinge 74 may be a flexible portion of the packaging 64, for example. An inside portion of the first cover 66 may include a recess 76 to receive the dial 11. Tabs 78 may extend vertically from the first cover 66. The tabs 78 may be adjacent to the recess 76 and may secure the first cover 66 to the base 72 by a press-fit. The tabs 78 may prevent rotation of the dial 11 while the first cover 66 remains on the base 72.

Figure 9:
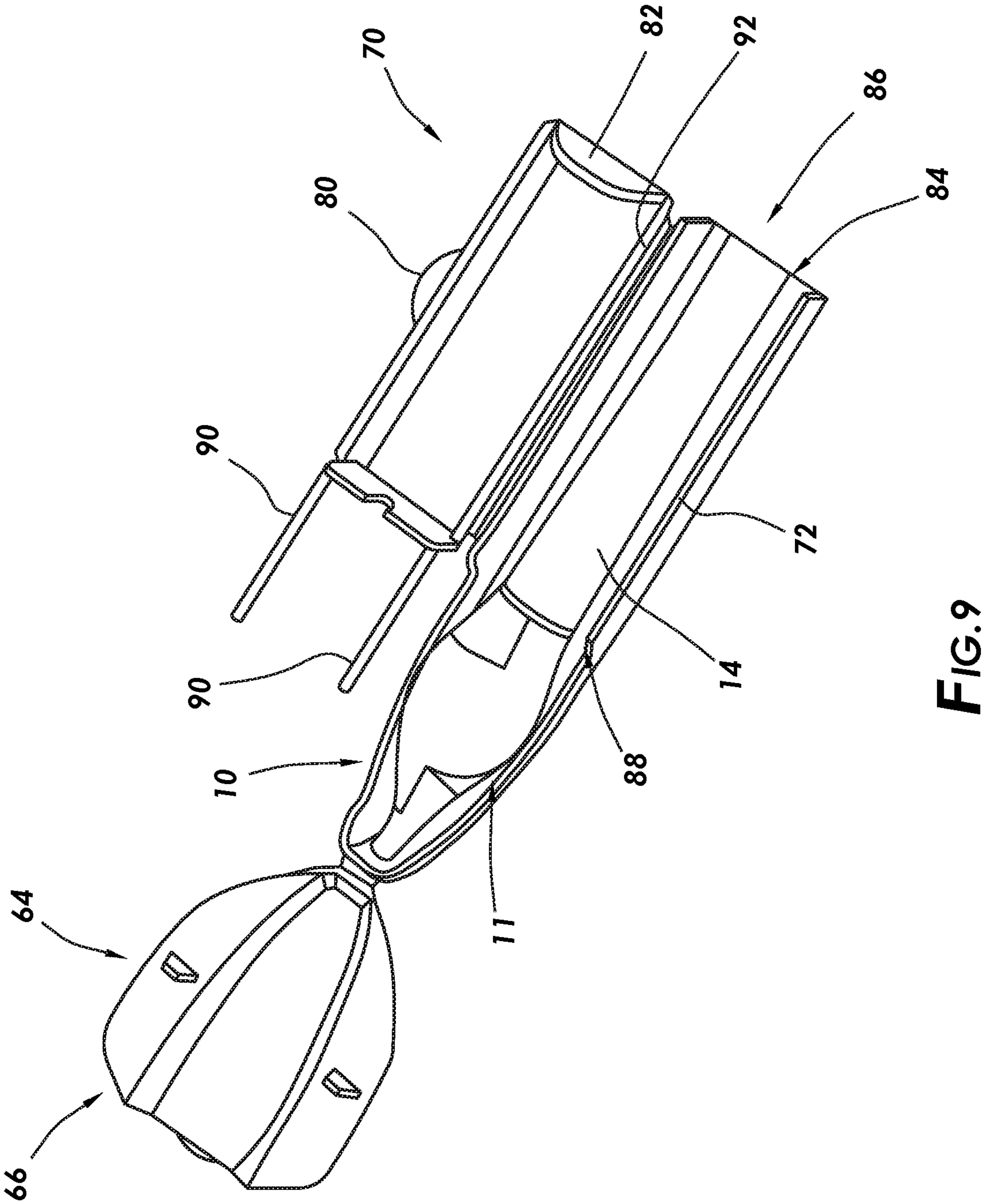
FIG. 9 illustrates a top view of the packaging of FIG. 7 with the first cover and a second cover removed to expose the dial and a plunger case of the IOL cartridge, in accordance with some embodiments of the present disclosure

FIG. 9 illustrates a top perspective view of the packaging 64 with the second cover 70 opened, in accordance with some embodiments of the present disclosure. The second cover 70 may be removed (e.g., pulled away) from the base 72 to expose the plunger case 14 of the IOL cartridge 10. The second cover 70 may include a tab 80 to assist a user with opening the second cover 70. The second cover may also include a projection 82 that aligns with an opening 84 of the base 72. The projection 82 extends into the opening 84 while the second cover 70 is closed, thereby providing a seal to prevent contamination of the IOL cartridge 10 during shipping and/or storage. The projection 82 and the opening 84 may be positioned at a proximal end 86 of the packaging 64. While the second cover 70 is removed from the base 72, the opening 84 is in fluid communication with an internal recess 88 of the base 72. The IOL cartridge 10 may be disposed within the internal recess 88.

Additionally, the second cover 70 may include prongs 90 that may be released from the internal recess 88 after the dial 11 has been rotated (e.g., 90°). The dial 11 may lock the second cover 70 in place until the dial 11 is rotated thereby allowing removal of the second cover 70. That is, the arms 22 prevent upward movement of the prongs 90 while the dial 11 is in the initial non-rotated position (e.g., shown on FIG. 8). The second cover 70 may be pivotably attached to a lateral hinge 92 positioned on a lateral side of the base 72.

In accordance with some embodiments, it should be noted that the first cover 66 is removed, then the dial 11 is rotated, and then the second cover 70 may be removed to retrieve the IOL cartridge 10 from the packaging 64. The particular configuration of the first cover 66, the second cover 70, and the dial 11 ensures that the IOL 16 (e.g., shown on FIG. 2) is folded before the IOL cartridge 10 is removably attached to a handpiece (not shown). After the first cover 66 and the second cover 70 are removed, the IOL cartridge 10 may be removed from the packaging 64.

Figure 10:
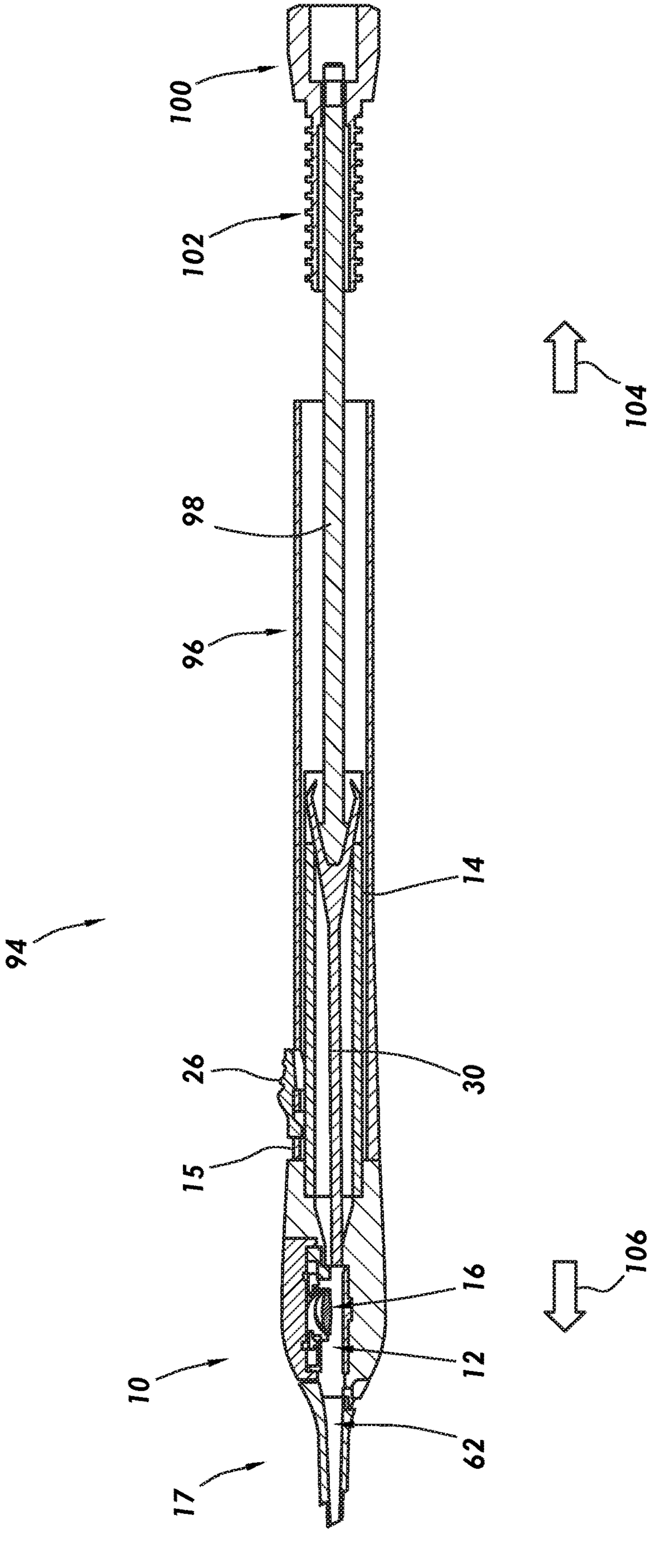
FIG. 10 illustrates the preloaded IOL cartridge of FIG. 1 removably attached to a handpiece.

FIG. 10 illustrates a side view cross-section of an insertion tool 94 that includes the IOL cartridge 10 removably attached to a handpiece 96 in accordance with particular embodiments of the present disclosure. The clip 26 may extend from the housing 15 of the IOL cartridge 10 to contact and secure against a portion the handpiece 96 thereby coupling the IOL cartridge 10 to the handpiece 96. A push rod 98 of the handpiece 96 may be actuated to advance the plunger 30 forward to deliver the IOL 16, in a folded state, from the compartment 12 through the passage 62 and the nozzle 17, and into a patient's eye. After delivery of the IOL 16, the nozzle 17 may be removed from the patient's eye, and the clip 26 may be pulled to disengage the IOL cartridge 10 from the handpiece 96. The used IOL cartridge 10 may then be disposed.

It should be noted that various handpieces may be used with different types of IOL cartridges. The handpiece 96 may include an electrically powered or a non-electrically powered drive mechanism that may include the push rod 98 extending along a length of the handpiece 96. The push rod 98 may be movably disposed within the handpiece 96 and may be manually actuated via a rotatable dial 100, which may cooperate with a fluid or a resilient member such as a spring 102 or another actuation mechanism. In general, for the purposes of discussing and describing the various components and features of the handpiece 96 and the IOL cartridge 10 of the IOL insertion tool 94, reference to a proximal end or direction may refer to a direction more towards an end of the handpiece 96 comprising the rotatable dial 100, according to directional arrow 104. Likewise, reference to a distal end or direction may refer to a direction more towards an end of the IOL cartridge 10 comprising the nozzle 17, according to directional arrow 106.

With reference to FIGS. 1-10, an exemplary technique for assembling the IOL cartridge 10 (e.g., shown on FIG. 1) to a handpiece 96 (e.g., shown on FIG. 10) to form the insertion tool 94 (e.g., shown on FIG. 10) in accordance with particular embodiments of the present disclosure is described as follows.

First, the packaging 64 containing the IOL cartridge 10 may be provided (e.g., see FIG. 7). Second, the first cover 66 of the packaging 64 may be at least partially removed from the base 72 of the packaging 64 (e.g., see FIG. 8) to expose the dial 11 of the IOL cartridge 10 that is disposed within the packaging 64. The IOL cartridge 10 may be preloaded with the IOL 16 (e.g., see FIG. 3) and the dial 11 of the IOL cartridge 10 is in an initial non-rotated state (e.g., see FIGS. 1 and 4) wherein the IOL 16 has not been folded. The positioning of the dial 11 in the initial non-rotated state may also prevent the prongs 90 of the second cover 70 of the packaging 64 from being moved or lifted, therefore preventing the second cover 70 from being prematurely opened to release the IOL cartridge 10 prior to folding of the IOL 16. Third, the dial 11 is rotated (e.g., 90°) thereby folding the IOL 16 (e.g., see FIG. 6), as previously discussed. Once the dial 11 is rotated, the prongs 90 of the second cover 70 may no longer be obstructed by the arms 22, and the prongs 90 may be moved or lifted. Fourth, the second cover 70 is pulled away from the base 72 of the packaging 64 to expose the plunger case 14 of the IOL cartridge 10 (e.g., see FIG. 9). Fifth, the IOL cartridge 10 is removed from the packaging 64 (e.g., see FIG. 5). The IOL cartridge 10 is then removably attached to a handpiece, such as handpiece 96, by sliding a portion of the plunger case 14 into the handpiece, and secured via the clip 26 (e.g., shown on FIG. 10) to form the insertion tool 94 (e.g., shown on FIG. 10). Upon actuation of the push rod 98 (e.g., shown on FIG. 10), the plunger 30 advances forward to deliver the IOL 16 from the compartment 12 through the nozzle 17.

To disassemble the insertion tool 94 (e.g., shown on FIG. 10) after delivery of the IOL 16, the clip 26 may be moved upward and held, thereby unlocking the IOL cartridge 10 from the handpiece 96 (e.g., see FIG. 10). Next, the IOL cartridge 10 may be pulled out from the handpiece 96 thereby sliding the plunger case 14 out from the handpiece 96.

Figure 11A:
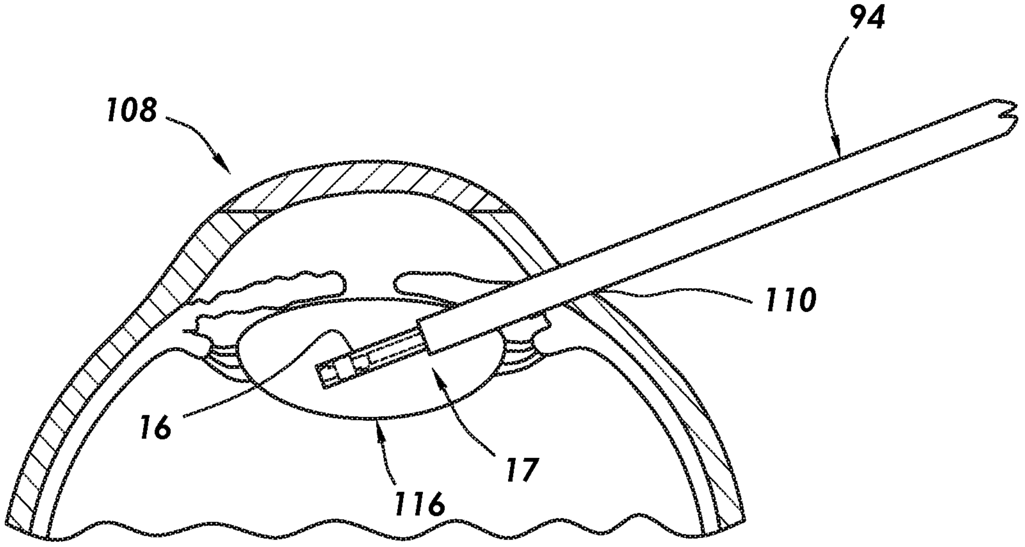
FIGS. 11A and 11B illustrate implantation of an IOL in accordance with some embodiments of the present disclosure.
Figure 11B:
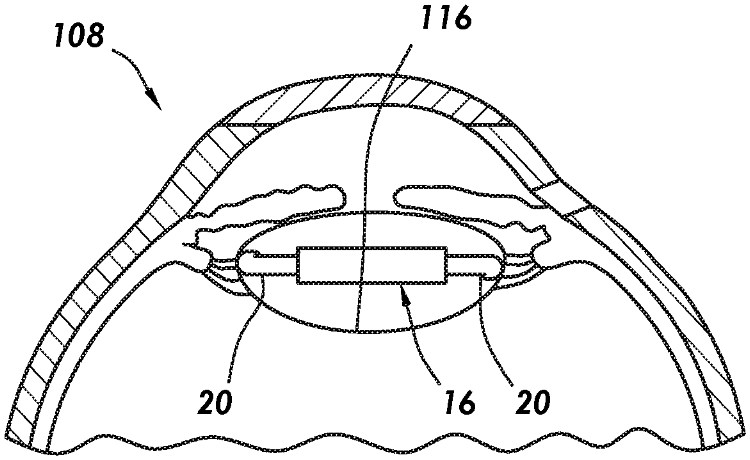

FIGS. 11A and 11B illustrate an exemplary technique for implantation of the IOL 16 into an eye 108 of a patient in accordance with particular embodiments of the present disclosure. An incision 110 may be made in the eye 108 by a surgeon. For example, the incision 110 may be made through the sclera of the eye 108. The incision 110 may be a suitable width or length. Without limitation, the suitable width and/or length may be less than 3 millimeters, and in some instances may be less than 2 millimeters. After the incision 110 is made, the nozzle 17 of the insertion tool 94 may be inserted through the incision 110 into a capsular bag 116 of the eye 108. The insertion tool 94 may be actuated to dispense the IOL 16 into the capsular bag 116 of the eye 108, as shown on FIG. 11B.

The IOL 16 may be delivered in a folded (or rolled configuration) and allowed to unfurl after ejection from the insertion tool 94. Upon dispensation, the IOL 16 should unfurl and settle within the capsular bag 116 of the eye 108, as shown on FIG. 11B. The haptic extensions 20 may be manipulated, for example, to engage an equator of the capsular bag 116. The haptic extensions 20 may engage the capsular bag 116 to secure the IOL 16 in the capsular bag 116.

Use of the methods and systems described herein may provide numerous benefits and advantages over other IOL delivery systems. For example, unpackaging of the IOL cartridge and folding of the IOL is streamlined, and a user is guided to complete the requisite steps in a specific order to ensure avoidance of errors and possible damage to or waste of costly IOLs and/or IOL cartridges. Additionally, the interchangeable utilization between different drive mechanisms and the preloaded IOL cartridge offers a simplified and uniform process for pairing drive mechanisms to preloaded IOL cartridges. Thus, a variety of handpieces employing different types of drive mechanisms may be used with each of numerous different types of IOL cartridges, and therefore different types of IOLs. For example, a user may readily select between multiple types of drive mechanisms he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

The invention claimed is:

1. A method for delivery of an intraocular lens (IOL), comprising:

opening a first cover of a packaging to expose a first portion of an IOL cartridge contained within the packaging, the IOL cartridge comprising a compartment comprising the IOL;

rotating a dial of the IOL cartridge to fold the IOL and unlock a second cover covering a second portion of the IOL cartridge, wherein the first cover and the second cover are aligned along a same longitudinal axis when closed;

opening the second cover; and removing the IOL cartridge from the packaging.

2. The method of claim 1, further comprising removably attaching the IOL cartridge to a handpiece comprising a push rod.

3. The method of claim 2, further comprising actuating the push rod to advance a plunger of the IOL cartridge through the compartment to move the IOL from the compartment out of the IOL cartridge.

4. The method of claim 1, wherein:

the rotation of the dial causes upward and inward movement of edge rollers pivotably disposed within the compartment; and the upward and inward movement of the edge rollers folds the IOL.

5. The method of claim 4, wherein the edge rollers further comprise tail portions configured to prevent backward rotation of the edge rollers during the upward and inward movement of the edge rollers.

6. The method of claim 5, wherein the tail portions being configured to prevent the backward rotation of the edge rollers during the upward and inward movement of the edge rollers comprises the tail portions being configured to contact and ride upward along tapered walls of the compartment during the upward and inward movement of the edge rollers.

7. The method of claim 1, wherein:

the rotation of the dial causes inward movement of compression arms extending into the compartment; and the inward movement of the compression arms folds or compresses haptic extensions of the IOL.

8. The method of claim 1, wherein the rotation of the dial causes:

upward and inward movement of edge rollers pivotably disposed within the compartment, wherein the upward and inward movement of the edge rollers folds the IOL; and inward movement of compression arms extending into the compartment, wherein the inward movement of the compression arms compresses haptic extensions of the IOL.

9. The method of claim 8, wherein the upward and inward movement of the edge rollers is simultaneous with the inward movement of the compression arms.

10. The method of claim 1, further comprising releasing prongs of the second cover once the dial has been rotated to unlock the second cover.

11. The method of claim 10, wherein arms of the dial are configured to prevent upward movement of the prongs while the dial is in an initial non-rotated position.

12. The method of claim 1, wherein the first cover is pivotably coupled to a base of the packaging by a hinge configured to facilitate the opening of the first cover.

13. The method of claim 1, wherein the second cover is pivotably coupled to a base of the packaging by a lateral hinge configured to facilitate the opening of the second cover.

14. A method for delivery of intraocular lenses (IOLs), comprising:

preventing removal of a first IOL cartridge from first packaging, the first IOL cartridge storing a first IOL;

folding the first IOL while the first IOL remains in the first IOL cartridge;

after folding the first IOL, removing the first IOL cartridge from the first packaging by:

opening a first cover of the packaging; and rotating a dial of the first IOL cartridge to unlock and open a second cover of the packaging, wherein the first cover and the second cover are aligned along a same longitudinal axis when closed;

attaching the first IOL cartridge to a handpiece comprising a drive mechanism;

actuating the drive mechanism to move the first IOL out of the first IOL cartridge;

removing the first IOL cartridge from the handpiece;

attaching a second IOL cartridge comprising a second IOL to the handpiece; and actuating the drive mechanism to move the second IOL out of the second IOL cartridge.

15. The method of claim 14, wherein:

the first IOL cartridge comprises a housing with a clip; and the handpiece comprises a portion configured to secure the clip to removably couple the first IOL cartridge to the handpiece.

16. The method of claim 15, wherein pulling the clip upward away from the handpiece enables removal of the first IOL cartridge from the handpiece.

17. The method of claim 14, wherein actuating the drive mechanism advances a plunger forward to move the first and second IOLs out of the first and second IOL cartridges, respectively, when the first and second IOL cartridges are respectively coupled to the handpiece.

18. The method of claim 14, wherein the first and second IOLs are moved out of the first and second IOL cartridges, respectively, in a folded state.

19. The method of claim 14, wherein the handpiece is reusable.

20. The method of claim 14, wherein the drive mechanism includes a non-powered drive mechanism actuated by one of pushing or screwing.

* * * * *